United States Patent [19]

Kurtz

[11] 4,044,068
[45] Aug. 23, 1977

[54] PROCESS AND APPARATUS FOR AUTOTHERMIC CRACKING OF ETHANE TO ETHYLENE

[75] Inventor: Bruce E. Kurtz, Marcellus, N.Y.

[73] Assignee: Allied Chemical Corporation, Morris Township, N.J.

[21] Appl. No.: 622,347

[22] Filed: Oct. 14, 1975

[51] Int. Cl.² .......................... C07C 5/42; C07C 5/44; C07C 5/48
[52] U.S. Cl. .............................. 260/683.3; 23/277 R; 208/130; 260/662 A; 260/683 R
[58] Field of Search ............ 260/683.3, 683 R, 662 A; 208/130; 48/DIG. 5; 23/277

[56] References Cited

U.S. PATENT DOCUMENTS

| | | | |
|---|---|---|---|
| 2,275,232 | 3/1942 | Rice | 260/683 |
| 2,315,499 | 4/1943 | Cantzler et al. | 260/683.3 |
| 2,394,851 | 2/1946 | Flett | 260/671 B |
| 2,397,638 | 4/1946 | Bell et al. | 260/683 |
| 2,423,493 | 7/1947 | Folkins | 260/683 |
| 2,769,772 | 11/1956 | Gomory | 208/130 |
| 3,336,412 | 8/1967 | Lyon et al. | 260/683.3 |
| 3,375,288 | 3/1968 | Rosset | 260/683.3 |
| 3,377,137 | 4/1968 | Latham | 260/662 A |
| 3,692,862 | 9/1972 | Staud et al. | 260/683 |

Primary Examiner—Delbert E. Gantz
Assistant Examiner—C. E. Spresser
Attorney, Agent, or Firm—Gerhard H. Fuchs; Anthony J. Stewart

[57] ABSTRACT

Process is provided for producing ethylene by the oxidative dehydrogenation ethane wherein a gas containing ethane is passed to a first elongated reaction zone, and a gas mixture containing oxygen and chlorine is passed into a second elongated gas zone positioned along said first gas zone, said first and second gas zones being separated by a porous member. The pressure of gases within the second gas zone is maintained in excess of the pressure in the first gas zone for diffusion of the chlorine and oxygen through the porous member into the first gas zone. The first gas zone is maintained under conditions sufficient to effect reaction therein of at least a portion of diffused oxygen and chlorine with ethane for production of ethylene. The reaction product containing the desired ethylene is discharged from the first gas zone.

11 Claims, 3 Drawing Figures

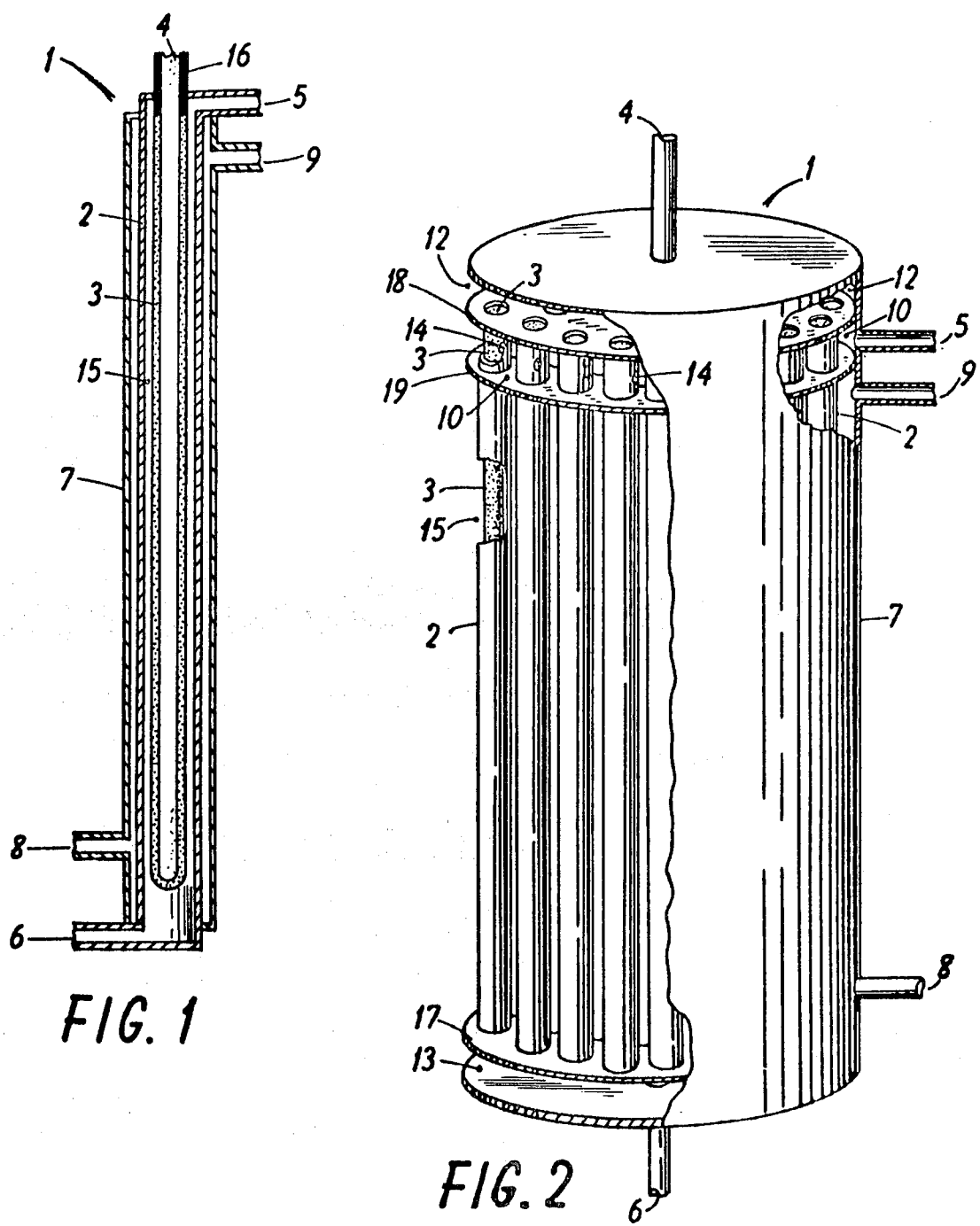

PROCESS FOR AUTOTHERMIC CRACKING OF ETHANE TO ETHYLENE

BACKGROUND OF THE INVENTION

1. FIELD OF THE INVENTION

This invention relates to process and apparatus for production of ethylene from ethane, and more particularly to the production of ethylene from ethane employing a porous tube reactor.

Processes have been developed for producing ethylene from ethane wherein ethane, oxygen and either elemental chlorine or a chlorine-containing reactant (e.g., HCl) are passed in contact with a catalyst at elevated temperatures for autotheric cracking (i.e., oxidative dehydrogenation) of ethane. See, e.g., U.S. Pat. Nos. 3,217,064; 3,278,627, 3,278,629; 3,278,630; 3,278,631; 3,308,183; 3,308,197; 3,658,933; 3,658,934; 3,702,311; and 3,862,996.

In the instance in which chlorine is used, the overall reaction of ethane, oxygen and chlorine to form ethylene, hydrogen chloride and water may be illustrated by the following equation:

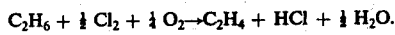

While such processes produce ethylene, the conversions are typically low, requiring recycle of large amounts of unreacted ethane, thereby leading to increased equipment costs and processing expenses. In addition, use of catalyst entails added expense due to the cost of the catalyst and to the need to periodically replace catalyst which has become poisoned or otherwise inactivated as a result of impurities present in the feed streams or from various by-products formed in the reaction. While processes such as that disclosed in U.S. Pat. No. 3,336,412 have been developed which do not employ catalyst, the pyrolysis product generally contains a substantial quantity of acetylene, therby complicating downstream recovery of the ethylene that is produced.

While generally less than about 1 weight percent of ethane fed to the reactor is converted to carbon, and thus while carbon formation does not seriously reduce the yield of ethylene, carbon depositions are disadvantageous due to the plugging of the reactor and downstream recovery equipment. While I do not wish to be bound by the theory given below, I believe that the carbon formation results from polymerization of acetylene which is in turn formed by the cracking of ethylene. The acetylene polymerization leads to formation of straight chains of increasing length whose condensation will ultimately form conjugated ring structures. Successive conjugations to form larger and larger conjugated ring structures at nucleation sites will ultimately lead to turbostratic carbon with platelets adhering to and aligned with the walls of reactor and exit lines. Continued growth of the straight chain acetylene polymers and homogenous dehydrogenation is believed to lead to amorphous carbon which is entrained in exit gases.

Thus, a process is desired which will provide ethylene from ethane while decreasing the amount of carbon deposits on process equipment.

Belgium Pat. No. 821,397, filed Oct. 23, 1974, discloses a process for preparation of ethylene dichloride and vinyl chloride from ethylene wherein the ethylene is produced by autothermic cracking of ethane.

SUMMARY OF THE INVENTION

According to the present invention, a process is provided for producing ethylene by the oxidative dehydrogenation of ethane which comprises (a) passing a gas containing ethane under pressure into a first elongted gas zone, (b) passing a gas mixture containing chlorine and oxygen under pressure into a second elongated gas zone positioned along said first gas zone, said first and second elongated gas zones being separated by a porous member, (c) maintaining the pressure of the gases in said second gas zone in excess of the pressure in said first gas zone for diffusion of oxygen and chlorine into said first gas zone, (d) maintaining said first gas zone under conditions sufficient to effect reaction therein of at least a portion of said diffused oxygen and chlorine with ethane for production of ethylene, and (e) withdrawing the gas product containing ethylene from said first gas zone.

The process of the present invention provides reaction between the chlorine, oxygen and ethane in the first gas zone adjoining the second gas zone as the ethane flows longitudinally through the first gas zone while the gas mixture containing chlorine and oxygen diffuses radially through the porous member which separates the two gas zones. The present invention has been found to result in ethylene yields per pass of up to 70% and more.

Apparatus for carrying out the process of the present invention are also provided and comprise an elongated housing provided with first and second elongated gas passages disposed therein, said first passage positioned substantially along said second passage and being separated therefrom by a porous member; means for introducing a first reactant gas into the first elongated gas passage; means for introducing a second reactant gas into the second elongated gas passage; means for maintaining the pressure in said second gas passage in excess of that within said first gas passage for substantially uniform diffusion of said second reactant gas from said second gas passage through said porous member to said first gas passage; means for maintaining said first gas passage under conditions sufficient to effect reaction therein of diffused oxygen and chlorine with ethane for production of ethylene; and outlet means for discharging the reaction mixture from said first gas passage. Heat exchange means for controlling the temperature within said first gas passage for reaction of said first and second reactant gases may also be provided.

BRIEF DESCRIPTION OF THE DRAWINGS

Preferred embodiments of the apparatus of the present invention are illustrated in the accompanying drawings wherein:

FIG. 1 is a longitudinal half section of one embodiment of the preferred apparatus of the present invention.

FIG. 2 is a perspective break-away view illustrating a preferred embodiment wherein a plurality of porous tube reaction units are combined for parallel action.

DETAILED DESCRIPTION OF THE INVENTION

Figure 3:
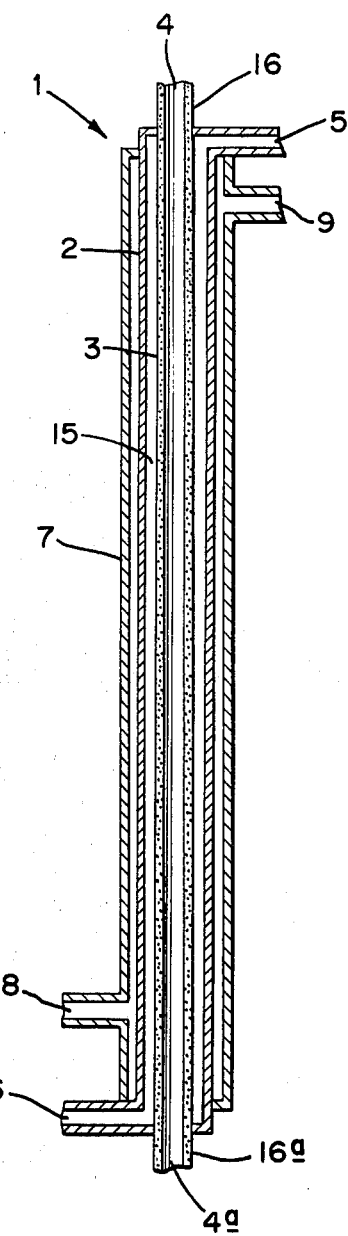
FIG. 3 is a longitudinal half section of a second embodiment of the preferred apparatus of the present invention.

The apparatus of the present invention comprises, in its broadest sense, an elongated housing provided with first and second elongated gas passages disposed therein. These passages are positioned substantially along one another and are separated by a porous member, for the major portion of their length so that the desired gases may pass from the second passage into the first passage along the major portion of the length of these elongated gas passages. The shape of the cross-section of the elongated first and second gas passages is not critical, and thus, these passages may be rectangular, circular or assymmetrical in cross-section. However, it is preferred that first and second gas passages be cylindrical, and hence of a circular cross-section.

In the preferred embodiment, the apparatus of the present invention comprises an elongated porous tube having an elongated gas zone disposed therein, and provided with gas inlet means for passing gas into said elongated gas zone; an outer elongated tube provided with substantially gas-impervious outer walls surrounding the porous tube and adapted to define an elongated annular gas zone internal to the outer tube and external to the porous member; means for introducing gas into the annular gas zone; means for maintaining the pressure in the elongated gas zone internal to the porous tube in excess of the pressure in the annular gas zone for diffusion of gas from the elongated gas zone into the annular gas zone, and outlet means for discharging gas from the annular gas zone. Heat exchange means for controlling the temperature within the annular gas zone may also be provided.

The apparatus of the present invention herein referred to as a porous tube reactor may be used as a single unit. Alternatively, one or more serially arranged units, or a plurality of unit reactors arranged for parallel operation, may be employed. In the preferred embodiment, a single unit of the porous tube reactor of the present invention comprises two concentric tubes with the inner tube being preferably closed at one end and being provided with a porous wall and an inlet for introducing a reactant gas therein. The outer tube is positioned about the inner tube to provide an annular space longitudinally therebetween and is provided with an inlet for a second reactant gas and an outlet for the gas reaction product. Optionally, heat transfer means can be associated with the outer tube.

In use, a gas mixture containing chlorine and oxygen, preferably as molecular chlorine and molecular oxygen, is introduced into into the inner tube and is diffused radially, and preferably substantially uniformly, into the annulus defined by the inner and outer tubes, reacting therein with a gas containing ethane introduced into the annulus. The ethylene reaction product is removed from the annulus through the outlet thereof. This outlet is generally positioned at a point removed from the inlet of the annulus. The reactor of this invention is specifically designed for adiabatic reaction temperatures and therefore the design is such that the reaction takes place in the annulus where temperature control to assure adiabatic conditions is possible. In addition to temperature control, the system, of which this reactor is a part, is also designed for careful control of such variables as flow rate, the proportion of reactants, residence time, and importantly, the degree of mixing in the annulus.

In the event a plurality of unit reactors is employed, they may be arranged for parallel operation in an outer casing with inlet and outlet ports, so that a heat transfer medium may circulate within the outer shell or jacket around the outer tubes of the plurality of units. Such an apparatus can be fabricated, for example, with a plurality of porous tube reactors spaced longitudinally within a containing casing.

Reference is now made to the accompanying drawings wherein like numerals indicate like or corresponding parts throughout the several views.

Referring to the porous tube reactor of FIG. 1, a plurality of which are also shown in the assembly of FIG. 2, the individual reactor comprises an outer tube 2, which is substantially gas impervious, an inner porous tube 3, a feed inlet for the gas mixture containing chlorine and oxygen 4, an inlet 5 for the gas containing the ethane reactant, a product outlet 6, and optionally, a jacket 7 for a heat transfer medium, said jacket having an inlet 8, and an outlet 9 for the heat transfer medium. The unit and the assembly comprising a plurality of these units should be resistant to chlorine and to HCl gas and the organic and chlorinated organic gases which may be formed as by-products.

FIG. 2 illustrates a preferred embodiment of the present invention wherein a bundle of porous tube reactor units are arranged in parallel, in this instance in a cylindrical container. There are several ways of this arrangement can be effected. In the method illustrated, there are two tube sheets, 18 and 19, at the upper end of the assembly and one tube sheet 17 at the lower end. These tube sheets are sealed along their periphery to the inner surface of the casing 7 to form two compartments or vestibules, 10 and 12, at the upper end of the assembly and one vestibule 13 at the lower end of the assembly. The outer impervous tubes are sealed into the bottom tube sheet 17 in the usual manner so that they then communicate with vestibule 13. The upper ends of these impervous tubes pass through and are sealed into tube sheet 19. The tubes then terminate at tube sheet 18, being sealed against the lower surface of the latter tube sheet. Since they are sealed to undersurface of tube sheet 18, the tubes do not communicate with vestibule 12 but surround the porous tube 3 which does so communicate. At least one opening, 14, is made in the impervous tube within the distance between tube sheet 18 and 19. With this arrangement, vestibule 12 is then in communication with vestibule 10 when one includes in the route of communication, the pores of the respective porous tubes. The short section of porous tube extending between tube sheets 18 and 19 is preferably rendered impervous as is also section 16 of the porous tube of FIGS. 1 and 3, and section 16a of the porous tube of FIG. 3.

In operation, a heat transfer medium such as hot combustion gases is introduced through inlet 8 of FIG. 1, and after circulating around impervous tube 2 exits at outlet 9. In the case of FIG. 2, there are no individual jackets surrounding impervous tubes 2 as in FIG. 1. Such individual jackets are not necessary as the heat transfer medium enters the casing at inlet 8, circulates all impervous tubes 2 and then exits at outlet 9. With respect to both FIG. 1 and FIG. 2, the gas containing chlorine and oxygen is introduced at inlet 4 and the gas containing ethane is introduced at inlet 5. In the embodiment of FIG. 3, the gas containing oxygen and chlorine is introduced to porous tube 3 at inlet 4 and that portion of this gas which does not pass through the porous walls into reaction zone 15, exits porous tube 3 at outlet 4a. In FIGS. 1 and 3 the gas mixture containing chlorine and oxygen diffuses substantially uniformly through porous wall 3 to react with ethane in annular zone 15 between porous tube 3 and impervous tube 2. Because of the substantially uniform introduction of the gas mixture containing chlorine and oxygen throughout the full length of the porous tube and the application of a heat transfer medium to the exterior wall of tube 2 to initiate the reaction and to supply or extract heat as required, essentially adiabatic reaction conditions in reaction zone 15 can be readily maintained if desired. The reaction product is removed from zone 15 through outlet 6. If desired, a portion, or all of this reaction mixture may be recycled for further cracking. In the apparatus of FIG. 2, a novel arrangement prevents the premature reaction between a portion of the reactants in vestibule 10. The ethane reactant entering vestibule 10 does not enter the impervous tubes at their intersection with tube sheet 19, but rather through perforations 14 in the side of the tubes. To further eliminate any opportunity for a portion of the reaction to occur within vestibule 10, that portion of the porous tube which extends between tube sheets 18 and 19 is rendered impervous.

The porous members separating the first and second gas passages in the apparatus of the present invention may be made of a wide variety of materials of construction. Vycor or quartz are quite satisfactory as materials of construction, although porous members made from alumina are preferred especially for large-scale operation. Thus, for example, porous Alundum, ceramic tubes or even a sintered metal tube, where compatible, may be used as porous tube 3 in the apparatus illustrated in FIG. 1. The purpose of the pores is to produce a substantially uniform diffusion of oxygen and chlorine into the first gas zone for reaction with ethane, thus enhancing high ethylene yields. Thus, it is preferred that the porosity of the porous member be substantially uniform along its length. The average pore diameter of the pores in the porous member may vary from greater than about 0.5 up to about 500 microns, with a range of from about 5 to 300 microns being preferred, and a range of from about 10 to 200 microns being most preferred. While porous members having an average pore size of less than 0.5 micron may be used, the pressures required for diffusion of gases therethrough make use of such low porosites undesirable.

For high ethylene yields it is preferred that inner zone 4 in porous member 3 be substantially cylindrical and be of a uniform cross-section, although such uniformity in cross-section is not critical. While porous tube 3 is closed at one end and open at the other end in the preferred embodiment, as shown in FIG. 1, this is not critical, and a porous tube may be employed which is open at both ends, provided the ethane-containing gas passing longitudinally out of inner zone 4 in such an embodiment does not pass into the annular reaction zone. FIG. 3 illustrates such an embodiment, wherein the gas containing oxygen and chlorine flows through porous tube 4 as indicated with recycle of non-diffused gases existing outlet 4a. In the operation of such an embodiment, the pressure of the gases within inner zone 4 will of necessity be greater than that required for an equivalent rate of diffusion to reaction zone 15 which would result from the operation of the apparatus of FIG. 1 wherein porous tube 3 is closed at one end.

The pressures employed in the first and second elongated gas zones (i.e., annular zone 15 and inner zone 4 in the apparatus of FIG. 1) are not critical and may vary widely. Thus, while pressures of from atomspheric to about 20 psig may be selected for ease of operation, pressures outside this range may also be used.

A graphite liner may be optionally provided along the inner surface of outer tube 2 to decrease the rate of formation of carbon deposits thereon (caused by reaction of the ethane, chlorine and oxygen in annular reaction zone 15) and to thereby provide increased conversions of ethane of ethylene.

To provide higher conversions of ethane to ethylene, it is preferred that the apparatus of the present invention be characterized by a length-to-diameter ratio of at least about 3:1, and more preferably at least 10:1. As used herein, the length-to-diameter ratio is defined as the ratio of (1) the inside length of the first elongated gas zone wherein the reaction of ethane to ethylene is effected, to (2) the average cross-sectional diameter of the first elongated gas zone. In the instance in which a porous tube reactor is employed, such as illustrated in FIG. 1, the inside length and inside diameter of outer tube 2 is used to compute this ratio.

Within the reactor, ethane is subjected to autothermic cracking in the presence of specified amounts of oxygen and chlorine, and under specified conditions of time and temperature. Cracking which does not require the continuous input of large quantities of heat is referred to herein as "autothermic" cracking. In conventional cracking of ethane to ethylene, an amount of heat must be supplied by the cracking equipment; on the other hand, in autothermic cracking, the large negative heat of formation of hydrogen chloride and water tends to balance the positive heat of formation of ethylene. Autothermic cracking minimizes heat input requirements, capital investment requirements, recycling, and by-product and carbon formation. This autothermic cracking operation comprises a step and a process for economic production of vinyl chloride and/or ethylene dichloride in high yield. The cracking step can be controlled so that only the hydrogen chloride actually required in the production of vinyl chloride and/or ethylene dichloride is formed. The raw materials are ethane, chlorine and oxygen. The oxygen can, if desired, be supplied entirely by air. High conversions of ethane ranging from about 20 to 90 percent with concomitant production of ethylene in yields, based on converted ethane, ranging from 100 to 70 percent can be obtained without the need for added catalytic agents.

In carrying out another preferred embodiment of the invention, chlorine, oxygen (or air) and ethane may be preheated by means of heat exchangers to a temperature preferably between 200° and 500° C before passage into the autothermic cracking zone. It is preferable to avoid temperatures above about 500° C for ethane so as to prevent thermal cracking and to avoid temperatures above 300° C for chlorine so as to protect the processing equipment from corrosion. At the elevated temperatures, chlorine becomes highly corrosive.

The reactants are maintained in the reaction zone for at least about 0.1 second, preferably from about 0.1 and 10 seconds, and most preferably from about 0.25 and 2.5 seconds, or for a time sufficient to convert concomitantly from about 20 to 95 percent of the ethane to 96 to 74 percent of ethylene, respectively, based on the converted ethane. Temperatures of from about 500° to 1,100° C. may be employed in the reaction zone, with temperatures of from about 700° to below about 1000° C. being preferred, and from about 850° to 950° c. being most preferred.

The conversion and yields obtained are greater at temperatures ranging from about 700° to below 1000° C. and retention times of from about 0.1 to 10 seconds than when the autothermic cracking step is carried out at temperatures in excess of 1000° C with retention times of less than 0.1 second. The percent conversion of ethane and the percent ethylene yield based on the ethane converted, bear approximately an inverse relationship.

The molar ratio of chlorine to ethane in the first elongated gas zone ranges preferably between about 0.1 and 2:1, more preferably from about 0.2 to about 1.2:1, and most preferably from about 0.4 to about 0.6:1. The chlorine to ethane molar ratio may be varied within the above range as desired to provide the excess of hydrogen chloride and unreacted ethane present in the product stream.

The molar ratio of the oxygen to ethane in the first elongated gas zone, wherein the autothermic cracking reaction is effected, is in the range of from about 0.001 to 0.5:1, preferably from about 0.005 to 0.5:1, and most preferably from about 0.1 to 0.4:1. The lower ratios improve the ethylene yield by reducing carbon monoxide and methane formation, but also decrease the rate of reaction. The use of these lower ratios requires that the reactants be preheated to a higher temperature. The residence time in the reactor itself is so short that little heat can be transferred there. However, the heat of reaction has been found to raise the reactants to the desired reaction temperature. If the oxygen-to-ethane ratio is adjusted downward to give a near zero heat of reaction, then the reactant preheat temperatures are preferably such that the desired reaction temperature is attained before introduction of the reactants into the reactor. In general, this is not very practical, so that the oxygen to ethane ratio is preferably kept high enough to give a significant temperature rise due to the heat of reaction. This temperature rise is increased by using substantially pure oxygen rather than air, so that required preheat temperatures are then reduced.

In addition to ethylene and hydrogen chloride products, various by-products of the autothermic cracking reaction are formed in minor quantities, including water, acetylene, methane, hydrogen and carbon monoxide in addition to elemental carbon. The by-products which account for the greatest reduction in yield are methane and carbon monoxide.

Thereafter, products of the reaction may be quenched, as by introducing a suitable quench liquid directly into the first elongated gas zone, after reaction is completed, to cool the exiting gases preferably to a reaction product temperature below about 600° C, and more preferably below about 500° C. Suitable quenching liquids include water, ethylene dichloride, and any other liquid which does not substantially react with the ethylene product. Water is the preferred quenching liquid. Thus, the exit end of the reactor may be fitted with a tube through which a quench liquid (e.g., water) is introduced directly into the reaction zone after reaction is complete. Alternative to (or in addition to) direct quenching, cooling coils and/or a cooling jacket may be placed about the end of the apparatus from which the product gases are withdrawn, for quenching of the product gases, preferably to a temperature below about 600° C. as indicated above. Rapid quenching has been found to aid in suppressing carbon formation and preventing reactor plugging.

The ethylene produced in the apparatus in accordance with the present invention may be recovered from the gases exiting the reactor by conventional means, and a discussion of ethylene recovery from these eixt gases is not necessary here.

Steam may be introduced in conventional amounts into the reactor either with the gas feed containing the ethane, or with the gas mixture containing oxygen and chlorine, or both, to further reduce carbon deposition on reactor walls and exit gas lines.

To remove any carbon which may have formed on reactor walls and exit gas lines, periodic decoking of the reactor may be necessary. In performing decoking, the flows of ethane and chlorine into the reactor are stopped, and an oxygen-containing gas, conveniently air, is allowed to pass through the reactor at elevated temperature, e.g. from about 900° to 1000° C., to oxidize the carbon deposits and to form gaseous oxidation products which are carried out of the reactor. The progress of the decoking process may be conveniently followed by gas chromatographic analysis of exit gases for carbon monoxide and carbon dioxide.

The process of the present invention may be further illustrated by reference to the following examples.

EXAMPLES 1 - 3

The reactor used in Examples 1 - 3 was an axial porous tube reactor having a 3 inch ID and being 17.5 inches long, and having an average pore size of 150 microns. The cylindrical chamber of the reactor had a volume of 2020 cubic centimeters (cc), and a length-to-diameter ratio (L/D) of 5.8. The chlorine and oxygen mixture was preheated to 200° C and was then passed into the reaction zone by means of a porous tube which entered the top of the cylindrical reactor, substantially aligned with the center axis of the reactor. This tube was closed at its lower end, and extended substantially the full length of the reaction zone. In the case of Examples 1 - 3, ethane was preheated to 600° C and was then introduced through a side tube into the top of the reaction zone. The ethane was therefore introduced into a cylindrical reaction zone positioned concentric to and surrounding the porous tube. The cylinder was fabricated of nickel and was provided with an inner graphite liner. A thermocouple extended into the reaction zone for temperature determination. The progress of the exothermic cracking step, and control of the operation was obtained by taking periodic samples for analysis. The operating conditions, yields and by-products are given in Table I. The high ethane conversions and ethylene yields should be noted.

TABLE I

| | | | EXAMPLES 1 - 3 | | | | |
|---|---|---|---|---|---|---|---|
| Ex. | Reactor Temp. ° C. | Ethane Feed g/m | $Cl_2/C_2H_6$ Mol Ratio | $O_2/C_2H_4$ Mol Ratio | $C_2H_4$ Conv. % | $C_2H_4$ Yield % | $C_2H_4$ Yield/pass % |
| 1 | 875 | 12.5 | 0.38 | 0.19 | 94.3 | 75.2 | 70.8 |
| 2 | 875 | 12.5 | 0.38 | 0.25 | 94.3 | 75.3 | 71.0 |
| 3 | 875 | 12.5 | 0.57 | 0.19 | 92.2 | 80.8 | 74.3 |

Other modes of applying the principle of the invention may be employed instead of those explained, changes being made as regards the method or compounds herein disclosed, provided the steps or compounds stated by any of the following claims, or the equivalent of said stated steps or compounds, be employed.

I claim:

1. A process for producing ethylene by the oxidative dehydrogenation of ethane which comprises (a) passing a gas containing ethane under pressure into a first elongated gas passage, (b) passing a gas mixture containing chlorine and oxygen under pressure into a second elongated gas passage positioned along said first gas passage, said first and second elongated gas passages being separated by a porous member, (c) maintaining the pressure of the gases in said second gas passage in excess of the pressure in said first gas passage for diffusion of oxygen and chlorine into said first gas passage, (d) maintaining said first gas passage under conditions sufficient to effect the reaction therein of at least a portion of said diffused oxygen and chlorine with ethane for production of ethylene, and (e) withdrawing the gas product containing ethylene from said first gas passage.

2. The process of claim 1 wherein the porous member is characterized by an average pore diameter of from greater than about 0.5 up to about 500 microns.

3. The process of claim 1 wherein the gas containing ethane and the gas mixture containing oxygen and chlorine are first introduced to the first and second elongated gas passages, respectively, at rates to provide a residence time of gas in said first passage of at least 0.1 second.

4. The process of claim 1 wherein the first gas passage is characterized by a length-to-diameter ratio of at least about 3:1.

5. The process of claim 1 wherein the first gas passage is maintained at temperature of from about 500° to about 1100° C.

6. The process of claim 1 wherein the first gas passage zone is maintained at a temperature of from about 700° to less than about 1000° C.

7. The process of claim 1 wherein the molar ratio of chlorine to ethane in the first gas passage is between about 0.1 and 2:1.

8. The process of claim 1 wherein the molar ratio of oxygen to ethane in the first gas passage is from about 0.001 to 0.5:1.

9. The process of claim 1 wherein the gas containing ethane is heated to a temperature of not greater than about 500° C. and the gas mixture containing oxygen and chlorine is heated to a temperature of not greater than about 300° C., prior to introducing said gases into their respective elongated gas passages.

10. The process of claim 1 wherein the first elongated gas passage is bounded along its length by a graphite member and said porous member.

11. The process of claim 1 wherein the first elongate gas passage is substantially annular and is located between said porous member and an impervious wall, said second elongated gas passage is disposed internally in said porous member which comprises a porous tube closed at one end and positioned at the core of said annular first gas passage.

* * * * *